(12) United States Patent
Beckman et al.

(10) Patent No.: US 8,905,914 B2
(45) Date of Patent: Dec. 9, 2014

(54) GASTRIC BAND DEVICE AND METHOD (75) Inventors: Andrew T. Beckman, Cincinnati, OH (US); Scott A. Woodruff, Cincinnati, OH (US)

(73) Assignee: Ethicon Endo-Surgery, Inc.

( * ) Notice: Subject to any disclaimer, the term of this patent is extended or adjusted under 35 U.S.C. 154(b) by 403 days.

(21) Appl. No.: 12/938,417

(22) Filed: Nov. 3, 2010

(65) Prior Publication Data

US 2012/0108892 A1 May 3, 2012

(51) Int. Cl.
*A61F 2/00* (2006.01)
*A61F 5/00* (2006.01)

(52) U.S. Cl.
CPC .............. *A61F 5/003* (2013.01); *A61F 5/0056* (2013.01); *A61F 5/0063* (2013.01); *A61F 2/004* (2013.01); *A61F 2002/0086* (2013.01); *A61F 2250/0003* (2013.01)
USPC ........................................................ 600/37

(58) Field of Classification Search
USPC .......... 600/29–31, 37; 606/151; 128/897–899
See application file for complete search history.

(56) References Cited

U.S. PATENT DOCUMENTS

| | | | |
|---|---|---|---|
| 5,152,770 A | 10/1992 | Bengmark et al. | |
| 5,910,149 A | 6/1999 | Kuzmak | |
| 6,067,991 A | 5/2000 | Forsell | |
| 6,461,292 B1 | 10/2002 | Forsell | |
| 6,470,892 B1 | 10/2002 | Forsell | |
| 7,416,528 B2 | 8/2008 | Crawford et al. | |
| 7,442,165 B2 | 10/2008 | Forsell | |
| 7,621,863 B2 | 11/2009 | Forsell | |
| 7,699,770 B2 | 4/2010 | Hassler, Jr. et al. | |
| 7,758,493 B2 | 7/2010 | Gingras | |
| 7,775,215 B2 | 8/2010 | Hassler, Jr. et al. | |
| 7,850,660 B2 | 12/2010 | Uth et al. | |
| 8,001,974 B2* | 8/2011 | Makower et al. | 128/898 |
| 8,317,677 B2 | 11/2012 | Bertolote et al. | |
| 8,360,955 B2 | 1/2013 | Sayet et al. | |
| 2006/0199997 A1 | 9/2006 | Hassler, Jr. et al. | |
| 2006/0211914 A1* | 9/2006 | Hassler et al. | 600/37 |
| 2007/0249894 A1 | 10/2007 | Nicholson | |
| 2007/0293716 A1* | 12/2007 | Baker et al. | 600/37 |
| 2008/0033548 A1* | 2/2008 | Xuenong et al. | 623/11.11 |
| 2008/0146868 A1 | 6/2008 | Henri Robert et al. | |
| 2008/0319435 A1 | 12/2008 | Rioux et al. | |
| 2009/0082618 A1 | 3/2009 | Abele et al. | |
| 2009/0216256 A1 | 8/2009 | Nicholson, IV et al. | |
| 2009/0306463 A1* | 12/2009 | Mouton et al. | 600/37 |

FOREIGN PATENT DOCUMENTS

| | | |
|---|---|---|
| EP | 0 923 356 | 6/1999 |
| FR | 2 921 822 | 4/2009 |

OTHER PUBLICATIONS

International Search Report dated Jun. 6, 2012 for Application No. PCT/US2011/058758.

* cited by examiner

*Primary Examiner* — Charles A Marmor, II
*Assistant Examiner* — Shannon McBride (57) ABSTRACT

An apparatus for forming a gastric restriction includes an implantable band and at least one tab. In some versions, the at least one tab may serve to stabilize the apparatus as it forms a gastric restriction. In some versions, an opening may be formed in the tabs such that sutures may be used. In some versions, a tissue scaffold and/or matrix may be used on the implantable band and/or the tabs to facilitate long term support for the implantable band, such as by substantially preventing the implantable band from sliding along an axis defined by an anatomical structure about which the implantable band is wrapped.

1 Claim, 8 Drawing Sheets

GASTRIC BAND DEVICE AND METHOD

BACKGROUND

A variety of systems and devices have been made and used for treating morbid obesity. Some such systems and devices include adjustable gastric band systems, which are operable to restrict the flow of food from the esophagus into the stomach. Some gastric bands include a fluid-filled elastomeric bladder with fixed endpoints that encircles the stomach just inferior to the gastro-esophageal junction. When fluid is added to the bladder, the band expands against the stomach, creating a food intake restriction or stoma in the stomach. To decrease this restriction, fluid is removed from the bladder. Examples of gastric bands are disclosed in U.S. Pat. No. 7,416,528, entitled "Latching Device for Gastric Band," issued Aug. 26, 2008, the disclosure of which is incorporated by reference herein. Another example of such an adjustable gastric band is disclosed in U.S. Pat. No. 6,067,991, entitled "Mechanical Food Intake Restriction Device," issued May 30, 2000, the disclosure of which is incorporated by reference herein.

To the extent that an adjustable gastric band system includes an injection port configured to receive the needle of a syringe assembly to add or withdraw fluid to or from the gastric band, those of ordinary skill in the art will appreciate that it may be desirable in some settings to locate both the injection port and, more specifically, the center of the injection port (e.g., when the septum of the injection port is at the center of the injection port). Locating the approximate center of the injection port with some degree of accuracy may facilitate addition or withdrawal of fluid via the injection port to adjust the gastric band system. One example of a system and method for identifying the location of an injection port is disclosed in U.S. Pub. No. 2006/0211914, entitled "System and Method for Determining Implanted Device Positioning and Obtaining Pressure Data" published Sep. 21, 2006, and issued Aug. 17, 2010 as U.S. Pat. No. 7,775,215, the disclosure of which is incorporated by reference herein.

Those of ordinary skill in the art will appreciate that it may be advantageous in certain circumstances to sense pressure, strain, and/or other parameters associated with operation of a gastric band device. In some settings, it may be desirable to obtain data indicative of the pressure of fluid in a gastric band. Various examples of methods and devices for obtaining pressure data and other types of data are disclosed in U.S. Pub. No. 2006/0189888, entitled "Device for Non-Invasive Measurement of Fluid Pressure in an Adjustable Restriction Device," published Aug. 24, 2006, and issued Apr. 20, 2010 as U.S. Pat. No. 7,699,770, the disclosure of which is incorporated by reference herein. Additional examples of methods and devices for obtaining pressure data and other types of data are disclosed in U.S. Pub. No. 2006/0199997, entitled "Monitoring of a Food Intake Restriction Device," published Sep. 7, 2006, and issued Sep. 13, 2011 as U.S. Pat. No. 8,016,745, the disclosure of which is incorporated by reference herein. Such parameter data may be obtained before, during, and/or after adjustment of a gastric band, and may be useful for adjustment, diagnostic, monitoring, or other purposes, and may also be obtained with respect to a mechanically actuated gastric band. In settings where a fluid-filled gastric band is used, pressure data may be used to determine whether the amount of fluid in the gastric band needs to be adjusted; and/or for other purposes.

In some instances, it will be appreciated that gastric bands may be difficult to use as a result of slipping post-installation. For example, the user may install a gastric band at a particular location, only to have the gastric band later slip or roll to an undesirable location. Such inadvertent movement of the gastric band may cause undesirable results and/or suboptimal treatment with the gastric band.

While a variety of gastric band systems have been made and used, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Gastric Band System

FIGS. 1-4 illustrate an exemplary gastric band system (10). As shown, gastric band system (10) comprises an injection port (12), a gastric band (20), and a catheter (18). Injection port (12) of the present example comprises a port housing (14) and a needle penetrable septum (16). Port housing (14) defines a fluid reservoir (not shown), such that a needle may pierce septum (16) to reach the reservoir and add or withdraw fluid (e.g., saline, etc.) as described in greater detail below. Port housing (14) may be formed of titanium, plastic, or any other suitable material or combination of materials. Septum (16) may be formed of silicone or any other suitable material or combination of materials. Injection port (12) may be subcutaneously secured over a patient's sternum, to the patient's abdominal fascia, or in any other suitable location. In some versions, injection port (12) is configured and operable in accordance with the teachings of U.S. Pub. No. 2005/0283118, entitled "Implantable Medical Device with Simultaneous Attachment Mechanism and Method," published Dec. 22, 2005, and issued Dec. 14, 2010 as U.S. Pat. No. 7,850,660, the disclosure of which is incorporated by reference herein. Alternatively, injection port (12) may have any other suitable configuration and/or operability.

Figure 1:
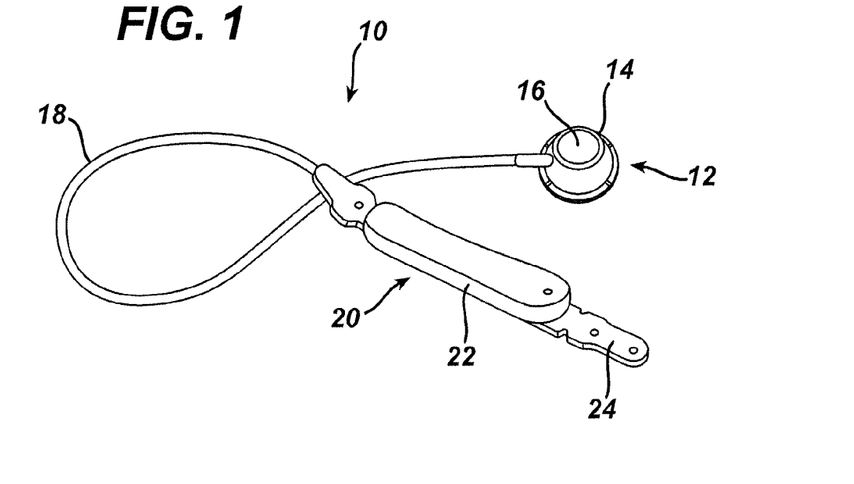
FIG. 1 depicts a perspective view of an implantable portion of an exemplary gastric band system.

Gastric band (20) of the present example comprises an inflatable bladder (22) that is secured to a flexible strap (24). Inflatable bladder (22) may be formed of silicone or any other suitable material or combination of materials. Catheter (18) provides fluid communication between bladder (22) and the reservoir of injection port (12). In the present example, catheter (18), bladder (22), and injection port (12) form a closed fluid circuit. Accordingly, a needle that is inserted through septum (16) may be used to add or withdraw fluid from inflatable bladder (22), to adjust the restriction created by gastric band (20) as described in greater detail below. In some versions, gastric band (20) is configured and operable in accordance with the teachings of U.S. Pat. No. 7,416,528, entitled "Latching Device for Gastric Band," issued Aug. 26, 2008, the disclosure of which is incorporated by reference herein. Alternatively, gastric band (20) may have any other suitable configuration and/or operability.

Figure 2:
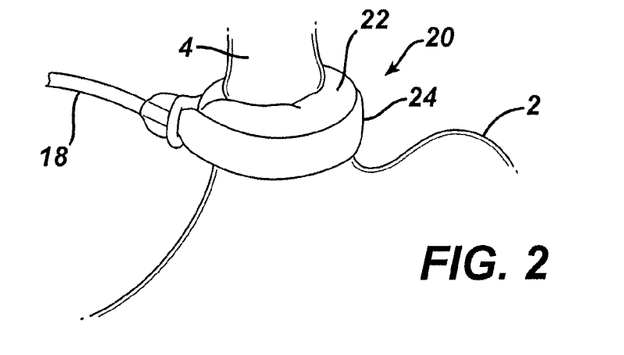
FIG. 2 depicts a perspective view of the gastric band of FIG. 1, showing the band positioned around the gastro-esophageal junction of a patient.

In some settings, gastric band (20) is applied about the gastro-esophageal junction of a patient. In particular, and as shown in FIG. 2, gastric band (20) is installed such that bladder (22) is adjacent to the tissue of the gastro-esophageal junction, with strap (24) on the outside of bladder (22). The ends of strap (24) are secured relative to each other when gastric band (20) is sufficiently wrapped about the patient's stomach (2). While strap (24) is flexible in this example, strap (24) substantially resists stretching along its length. Accordingly, when fluid is added to bladder (22) (e.g., using a needle inserted through septum (16) of injection port (12), etc.), bladder (22) expands and exerts inward forces on the gastro-esophageal junction of the patient. This reduces the size of the internal stoma at the gastro-esophageal junction, thereby creating a restriction on food intake into the patient's stomach (2). It should be understood that the size of this stoma may be decreased by adding more fluid to bladder (22) to create a greater degree of restriction; or increased by withdrawing fluid from bladder (22) to reduce the degree of restriction.

Figure 3:
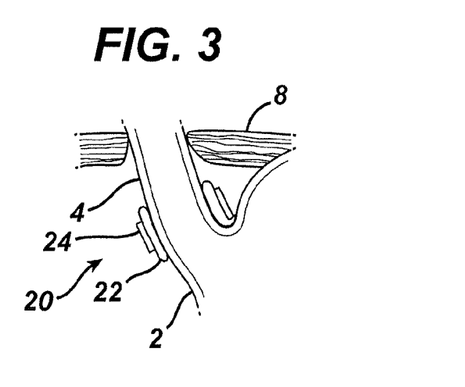
FIG. 3 depicts a cross-sectional view of the gastric band of FIG. 1, showing the band positioned around the gastro-esophageal junction of a patient in a deflated configuration.
Figure 4:
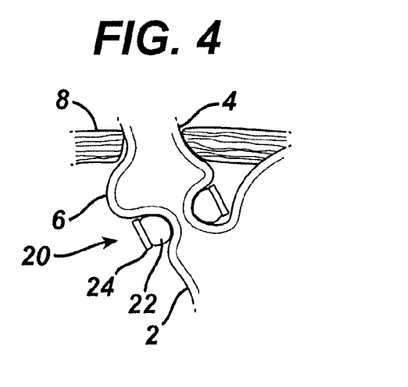
FIG. 4 depicts a cross-sectional view of the gastric band of FIG. 1, showing the band positioned around the gastro-esophageal junction of a patient in an inflated configuration to create a food intake restriction.

As shown in FIGS. 2-4, an installed gastric band (20) at least substantially encloses the upper portion of stomach (2) near the junction with esophagus (4) in the present example. FIG. 3 shows gastric band (20) in a deflated configuration, where bladder (22) contains little to no fluid, thereby maximizing the size of the stoma opening into stomach (2). FIG. 4 shows gastric band (20) in an inflated, fluid-filled configuration, where bladder (22) contains substantially more fluid than is shown in FIG. 3. In this configuration shown in FIG. 4, the pressure of gastric band (20) against stomach (2) is increased due to the fluid within bladder (22), thereby decreasing the stoma opening to create a food intake restriction. FIG. 4 also schematically illustrates the dilation of esophagus (4) above gastric band (20) to form an upper pouch (6) beneath the diaphragm muscle (8) of the patient.

II. Gastric Band Variations

It will be appreciated that in some versions, a variation of a gastric band may be desired for use with gastric band system (10). Upon using gastric band (20) such as one depicted in FIGS. 1-4, in some configurations and/or installations, gastric band (20) may be prone to undesirable slipping, rolling, or otherwise failing to maintain a desired location on the esophagus or stomach. Furthermore, it will be appreciated that in some settings, simply a different sort or configuration of gastric band may be desired.

Figure 5:
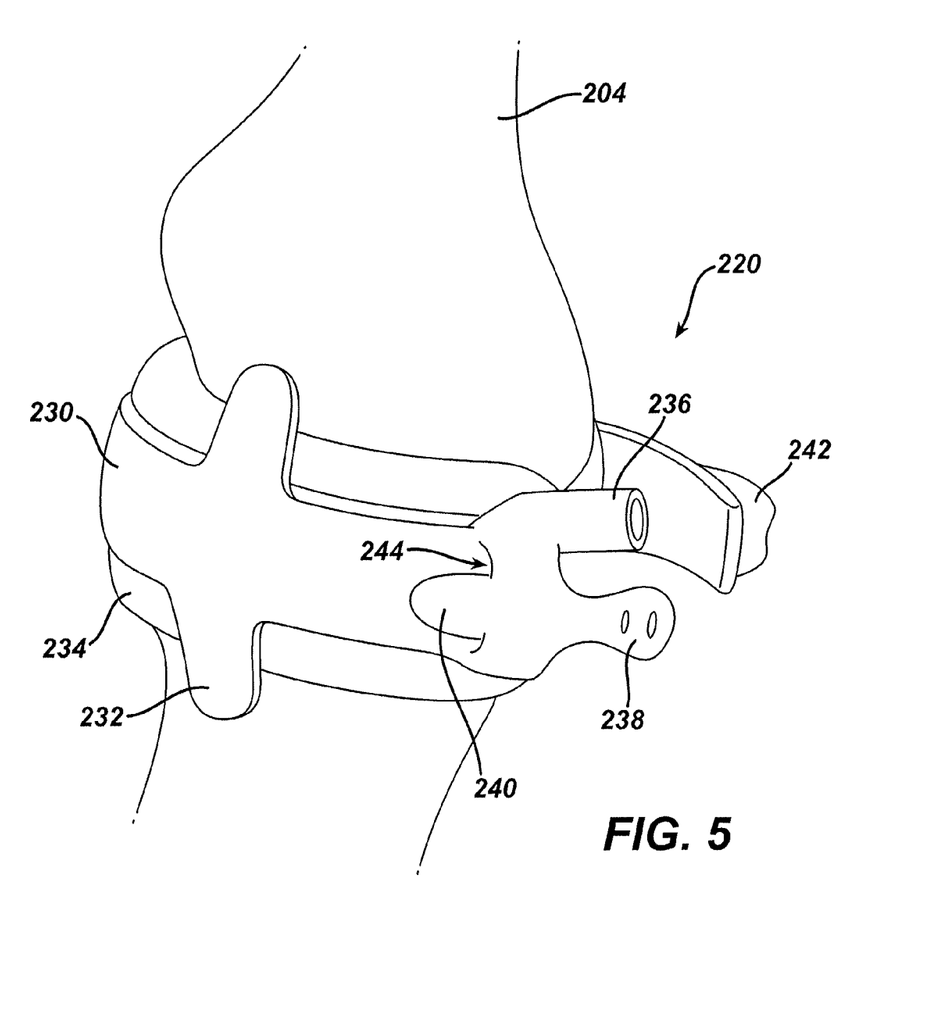
FIG. 5 depicts a perspective view of an alternative version of a gastric band wrapped around a portion of the digestive tract of a patient.
Figure 6:
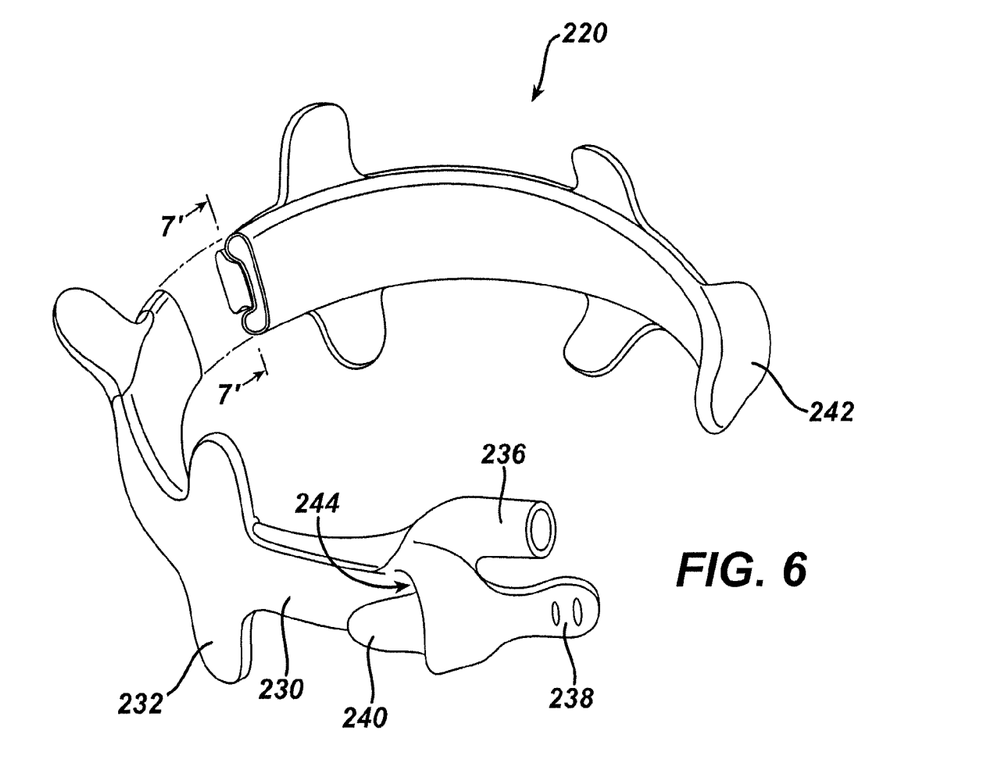
FIG. 6 depicts another perspective view of the gastric band of FIG. 5.
Figure 7:
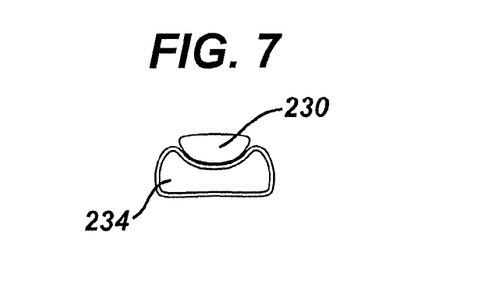
FIG. 7 depicts a cross sectional view of the gastric band of FIG. 5, taken along line 7'-7' of FIG. 6.

FIGS. 5-7 depict an exemplary version of a gastric band (220). Gastric band (220) may be used to wrap around an esophagus (204) or stomach. Gastric band (220) of this example comprises an outer band (230) and an inner band (234). Gastric band (220) further comprises a fluid port (236).

Outer band (230) is sized to fit around the outside of inner band (234). Both outer band (230) and inner band (234) are sized to wrap around a portion of esophagus (204). Alternatively, outer band (230) and inner band (234) may fit around a stomach rather than a portion of esophagus (204). Outer band (230) comprises a generally flexibly rigid biocompatible material, but any suitable material may be used as would be apparent to one of ordinary skill in the art in view of the teachings herein Inner band (234) comprises an inflatable portion such that inflating inner band (234) forms a gastric restriction. A plurality of tabs (232) are connected to outer band (230). Tabs (232) may be integrally formed into outer band (230), may be attached after outer band (230) is constructed, or may be of unitary construction with outer band (230). Tabs (232) have a rounded, wing-like shape extending outwards from outer band (230). However, tabs (232) may have any shape as would be apparent to one of ordinary skill in the art in view of the teachings herein. In the illustrated version, tabs (232) are symmetrically positioned on opposite sides of outer band (230). In relation to each other, pairs of tabs (232) are distributed equally along the length of outer band (230). In some alternative versions, tabs (232) may be positioned in different arrangements along outer band (230). Tabs (232) are further shaped so as to slope gently towards the ends of tabs (232). Furthermore, tabs (232) may be rigidly flexible. That is, tabs (232) may be flexible enough such that through use, no inadvertent damage is caused to the stomach; yet rigid enough to provide stability to gastric band (220). Tabs (232) may further comprise a variety of textures such as a ribbed or bumped outer surface. However, any suitable texture for tabs (232) may be used. It will be appreciated that tabs (232) may aid in stabilizing gastric band (220). Tabs (232) may also comprise other features, some examples of which will be discussed in more detail below.

As mentioned above, gastric band (220) also comprises inner band (234) Inner band (234) comprises a band having a width that is wider than outer band (230). However, any suitable width for inner band (234) may be used as would be apparent to one of ordinary skill in the art in view of the teachings herein. For example, inner band (234) may have a width narrower or even identical to outer band (230). Outer band (230) and inner band (234) may be connected to each other through an overmolding process or adhesive, or any other suitable means. For example, FIG. 7, which shows a cross section taken at line 7'-7' of FIG. 6, shows how outer band (230) and inner band (234) may be positioned in relation to each other Inner band (234) comprises a slight recess to fit outer band (230).

Gastric band (220) of the present example further comprises an end tab (238). End tab (238) is positioned at the end where gastric band (220) terminates, and end tab (238) may be grasped by a user to aid in positioning of gastric band (220). End tab (238) comprises a textured surface comprising, for example, horizontal ribs to enable a user to more easily grasp end tab (238). End tab (238) may be used while gastric band (220) is being wrapped around esophagus (204) or a portion of stomach. For example, as gastric band (220) is positioned to wrap around a portion of esophagus (204), the user may then grasp end tab (238) to pull gastric band such that it encircles esophagus (204) or a portion of the stomach.

Gastric band (220) further comprises a tongue (240) and an end engagement portion (242). Tongue (240) is positioned near end tab (238). Tongue (240) is further positioned such that it faces away from end tab (238). Tongue (240) is shaped generally as a curved, blunt hook. The curve of tongue (240) is shaped such that tongue (240) generally matches the outer curvature of outer band (230). However, tongue (240) may comprise any suitable shape as would be apparent to one of ordinary skill in the art in view of the teachings herein.

End engagement portion (242) has a curved cup-like shape and is positioned at the end of gastric band (220) on the opposing end from end tab (238). End engagement portion (242) is configured such that the cup defined by end engagement portion (242) receives tongue (240) when end engagement portion (242) is pulled through opening (244). With tongue (240) inserted in the cup of end engagement portion (242), this engagement provides sufficient strength such that gastric band (220) will substantially maintain its position on esophagus (204) without loosening substantially. However, end engagement portion (242) and end tongue (240) need not be locked together such that if gastric band (220) should require removal, gastric band (220) may be unbuckled by the user by pushing end engagement portion (242) further away from tongue (240) to disengage tongue (240) from the cup of end engagement portion (242), then pulling end engagement portion (242) back through opening (244). However, in other alternative versions, tongue (240) and end engagement portion (242) may form a more permanent lock. In some versions, end tab (238) may be looped through an opening, which may further be used to affix gastric band (220) around the stomach. It should also be understood that end tab (238), tongue (240), and engagement portion (242) may be constructed and operable in accordance with the teachings of U.S. Pat. No. 7,416,528, the disclosure of which is incorporated by reference herein.

Gastric band (220) further comprises fluid port (236). Fluid port (236) may provide fluid communication from gastric band (220) to a catheter (not shown) and ultimately an injection port (not shown). In the illustrated version, fluid port (236) is in communication with inner band (234), which inflates or deflates based on the amount/direction of fluid communicated through fluid port (236). However in other versions, fluid port (236) may be in communication with any portion of gastric band (220) that expands.

In conjunction with a catheter and injection port, a fluid, such as saline, may be added to injection port. As fluid flows into gastric band (220) gastric band (220) becomes inflated thereby causing gastric band (220) to inwardly inflate. As a result a gastric restriction is formed. As gastric band (220) inwardly inflates, tabs (232) may adjust through inflation of gastric band (220) such that tabs provide sufficient stability to gastric band (220).

Figure 8:
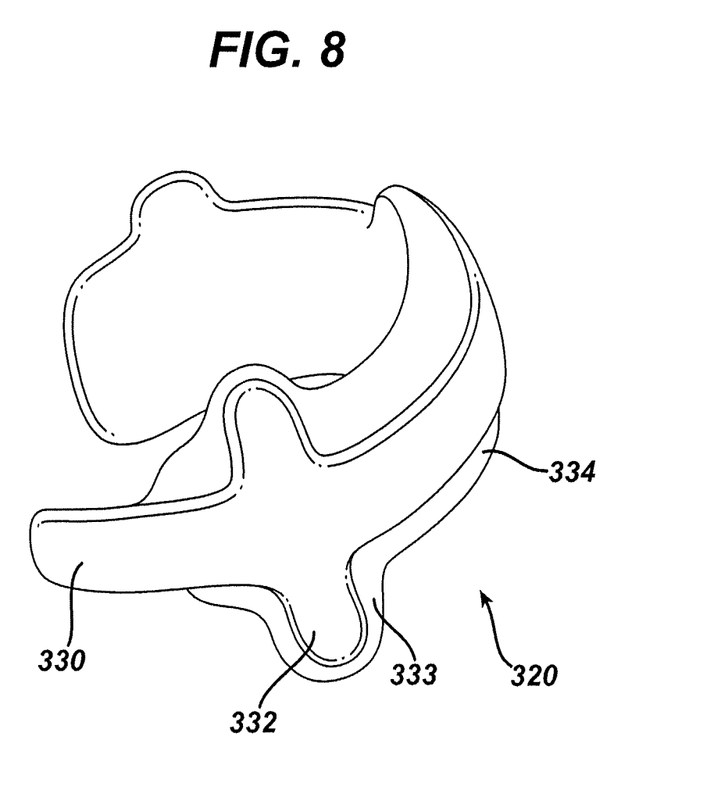
FIG. 8 depicts a perspective view of an yet another alternative version of a gastric band.

FIG. 8 depicts a gastric band (320) having only an inner band (334), an outer band (330), and a plurality of tabs (332). In the illustrated version, in addition to tabs (332) on outer band (330), inner band (334) also comprises wings (333) that extend similarly to tabs (332). Wings (333) may have a shape that conforms to tabs (332) or alternatively, wings (333) may have any shape as one of ordinary skill in the art may find suitable in view of the teachings herein.

Figure 9:
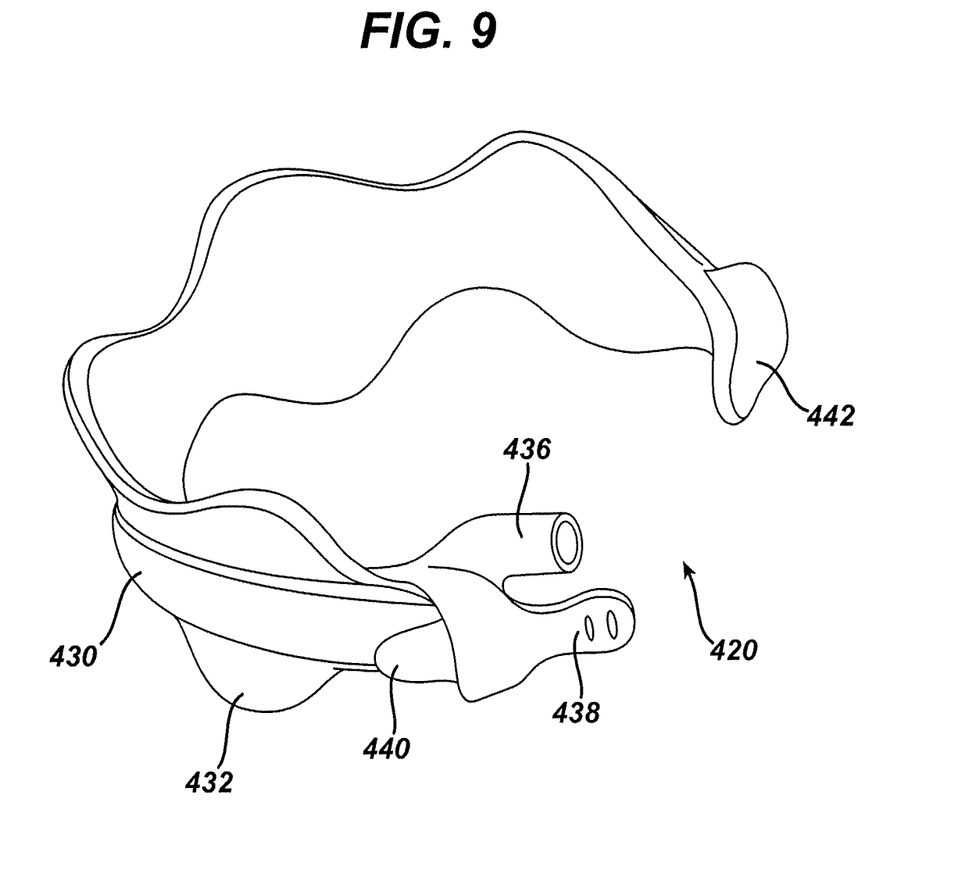
FIG. 9 depicts a perspective view of yet another alternative version of a gastric band.

FIG. 9 depicts an alternative version of a gastric band (420) comprising an outer band (430), an inner band (432), a tongue (440), an end tab (438), an end engagement portion (442), and a fluid port (436). In the illustrated version, inner band (432) comprises a plurality of tabs (432), which may be used to stabilize gastric band (420) once gastric band (420) is placed on an esophagus or stomach. Tabs (432) are shaped to have a wider, wing-like shape thereby providing further stability for gastric band (420). However, tabs (432) may have any suitable shape as would be apparent to one of ordinary skill in the art in view of the teachings herein. Because tabs (432) are part of inner band (432), as inner band (432) inflates, tabs (432) also inflate, which enables a wider surface area for inner band (432) to engage an esophagus or stomach to maintain stability or maintain a desired location for gastric band (420).

Figure 10:
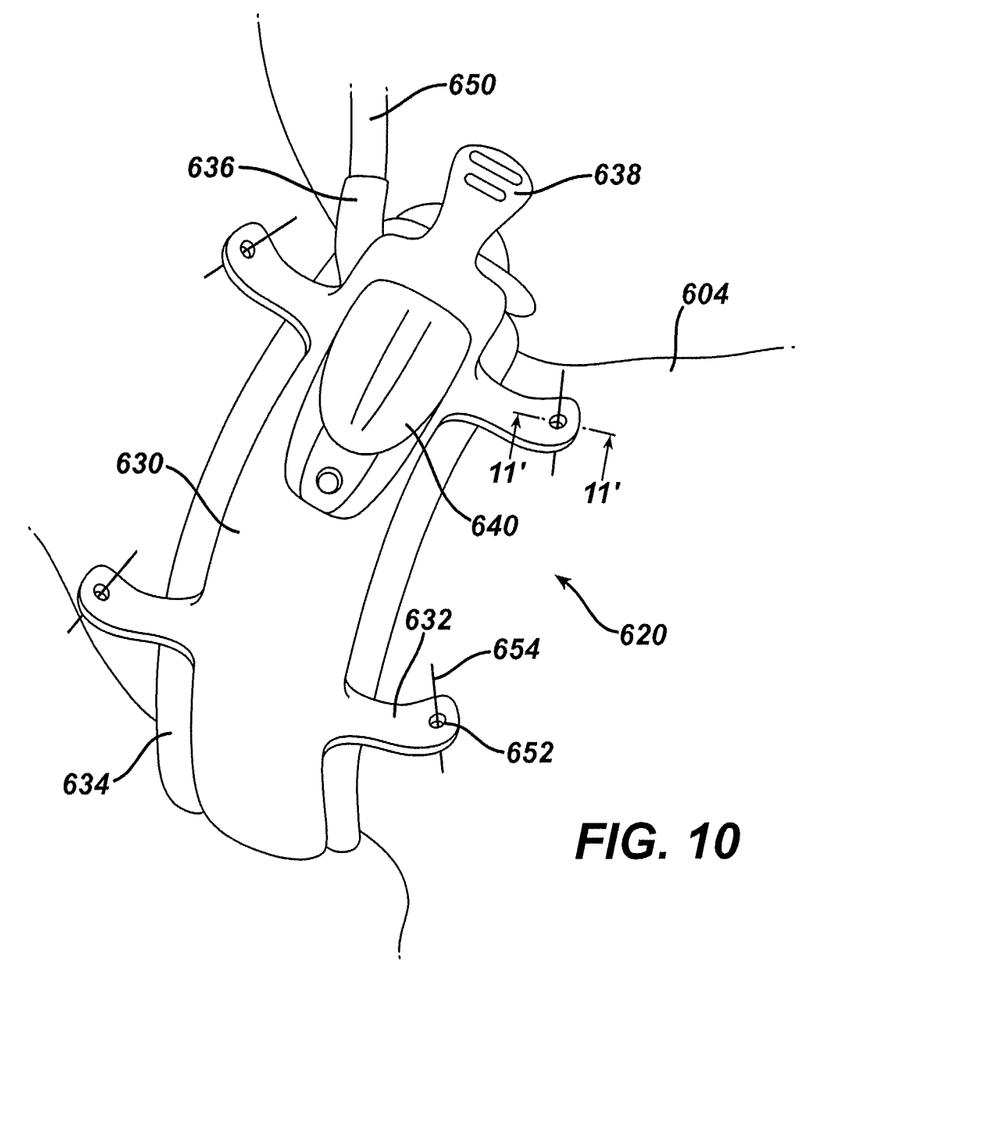
FIG. 10 depicts a perspective view of yet another alternative version of a gastric band.

FIG. 10 shows another alternative version of a gastric band (620). Gastric band (620) comprises an inner band (634), an outer band (630), a tongue (640), an end tab (638), and a fluid port (636). Gastric band (620) further comprises a plurality of tabs (632). Tabs (632) have a rounded, narrow shape and extend outwardly from inner band (634). An opening (652) is formed in the center of each tab (632). Each opening (652) may be used to secure gastric band (620) to an esophagus (604) by inserting suture thread (654) through opening (652) to attach gastric band (620) to esophagus (604) or a portion of stomach. In the illustrated version, opening (652) is placed generally in the center of tabs (632). However, any suitable position for opening (652) may be used. In addition, opening (652) may not necessarily be limited to a single opening (652). Multiple openings may be used as one of ordinary skill in the art might find suitable in view of the teachings herein. It should also be understood that tacks, staples, and/or various other devices may be inserted through openings (652) to secure gastric band (620) in place. In some versions, each tab (632) includes a respective overmolded suture loop (not shown), in lieu of openings (652), to provide tie-downs. Such suture loops may be formed of bioabsorbable material and/or material(s) having any other suitable properties.

Figure 11:
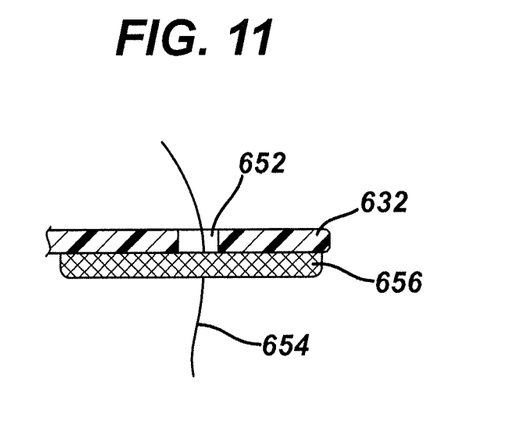
FIG. 11 depicts a cross sectional view of a tab of the gastric band of FIG. 10, taken along line 11'-11' of FIG. 10.

FIG. 11 depicts a cross section taken along line 11'-11' of one of tabs (632) shown in FIG. 10 comprising an opening (652) extending through the center of tab (632). On the bottom portion of tabs (632) is a tissue in-growth matrix (656). Tissue in-growth matrix (656) may be attached to tabs (632) by a biosurgical adhesive such as RTV. Tissue in-growth matrix (656) comprises a matrix that may be infused with, for example, tissue or stem cell materials, in a slurry form or other form, to facilitate tissue growth. In addition or in the alternative, tissue in-growth may be promoted by providing a porous surface treatment matrix made of a material such as silicone. Of course, tissue in-growth matrix (656) need not necessarily be infused with stem cells or anything else, and may simply provide a structure configured to promote tissue in-growth (e.g., trabeculae, pores, mesh, etc.), Tissue in-growth matrix (656) may comprise, for example, a Neoform mesh material or, for example, a Seare® BioMatrix System. Tissue in-growth matrix (656) material generally may be selected such that stomach or esophageal tissue may become integrated with tissue in-growth matrix (656) over the time span of, for example, several weeks. Sutures (654) used to attach tabs (632) to stomach or esophageal tissue may be selected such that sutures biodegrade over the time span of several weeks. Thus, sutures (654) may be used temporarily to hold gastric band (620) in place while over time, tissue in-growth matrix (656) integrates with tissue. Then, as sutures (654) dissolve, tissue in-growth matrix (656) integrates with tissue sufficiently such that sutures (654) are no longer necessary for providing stability for gastric band (620). Thus, rather than having to remove sutures (654) later, a biodegradable material may be used for sutures (654) without concern as to whether gastric band (620) will maintain a desirable location. Furthermore, tissue in-growth with tissue in-growth matrix (656) as well as elastomeric flexibility of tabs (632) may allow for a more natural movement type of connection as opposed to a more rigid connection that might be encountered using some other form of securing gastric band (620). Tissue in-growth matrix (656) may be positioned such that it covers opening (652) or tissue in-growth matrix (656) may shaped to have an opening that matches or otherwise complements opening (652) of tabs (632). In the illustrated version, tissue in-growth matrix (656) is positioned only on tabs (632) such that if gastric band (620) needs to be removed in the future, only the portions where tissue in-growth matrix (656) is connected to tissue needs to be cut. Then, gastric band (620) may be removed.

Figure 12:
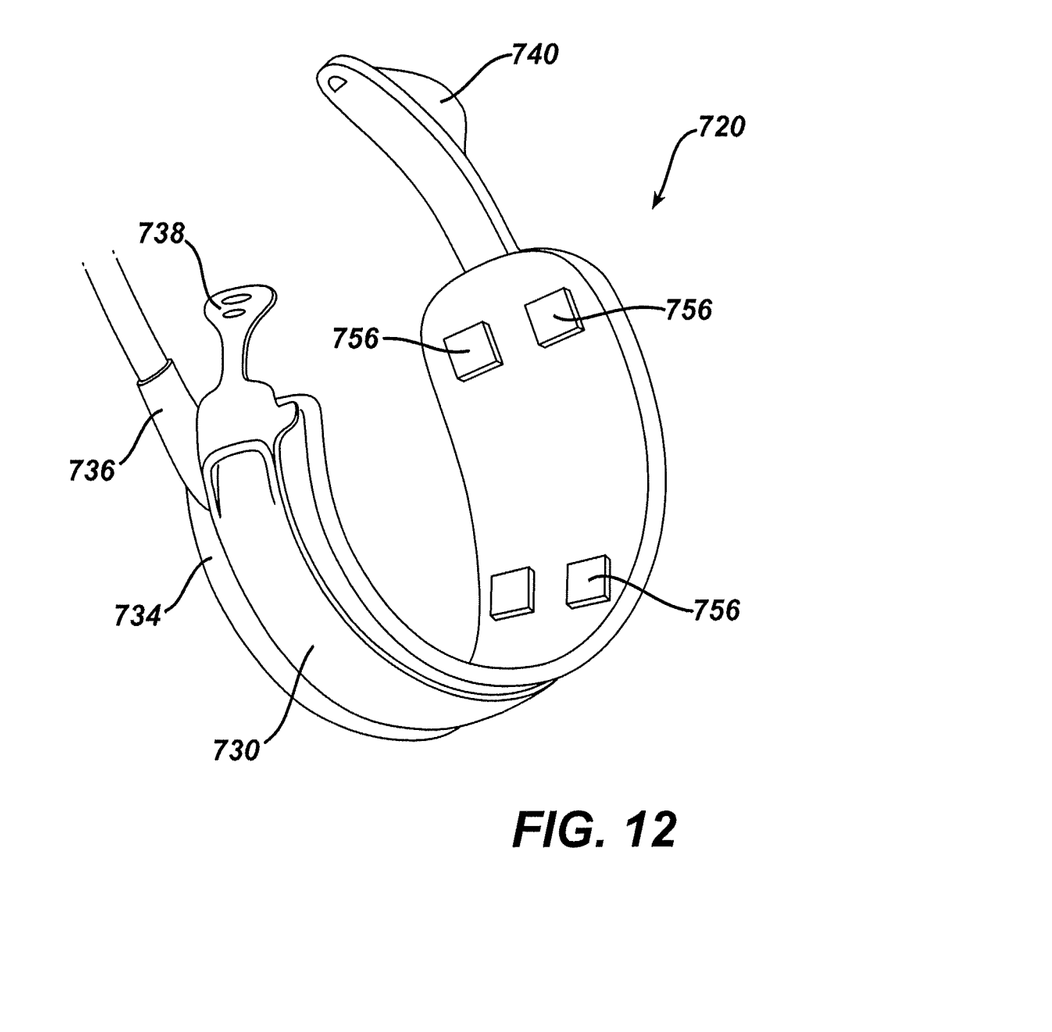
FIG. 12 depicts a perspective view of yet another alternative version of a gastric band.

FIG. 12 depicts yet another alternative version of a gastric band (720). Gastric band (720) comprises an outer band (730) and an inner band (734). Gastric band (720) further comprises an end tab (738), a pull tab (740), and a fluid port (736). Gastric band (720) comprises a plurality of tissue in-growth matrix patches (756). In the illustrated version, tissue in-growth matrix patches (756) are positioned along the inner surface of inner band (734) such that when gastric band (720) is positioned on stomach or esophagus, patches (756) may gradually integrate with surrounding tissue over time. Patches (756) are generally square-shaped in the present example, but any suitable shape may be used as would be apparent to one of ordinary skill in the art in view of the teachings herein. Furthermore, patches (756) may be spaced apart evenly along the inner portion of inner band (734). However, any suitable position for patches may be used as would be apparent to one of ordinary skill in the art in view of the teachings herein. For example, a higher concentration of patches (756) may be used in an area where gastric band (720) may be particularly susceptible to slipping.

It will become readily apparent to those skilled in the art that examples described herein may have applicability to other types of implantable bands. For example, bands are used for the treatment of fecal incontinence. One such band is described in U.S. Pat. No. 6,461,292, entitled "Anal Incontinence Treatment with Wireless Energy Supply," issued Oct. 8, 2002, the disclosure of which is incorporated by reference herein. Bands can also be used to treat urinary incontinence. One such band is described in U.S. Pat. No. 7,621,863, entitled "Urinary Incontinence Treatment with Wireless Energy Supply," issued Nov. 24, 2009, the disclosure of which is incorporated by reference herein. Bands can also be used to treat heartburn and/or acid reflux. One such band is described in U.S. Pat. No. 6,470,892, entitled "Mechanical Heartburn and Reflux Treatment," issued Oct. 29, 2002, the disclosure of which is incorporated by reference herein. Bands can also be used to treat impotence. One such band is described in U.S. Pat. No. 7,442,165, entitled "Penile Prosthesis," issued Oct. 28, 2008, the disclosure of which is incorporated by reference herein. Various ways in which the teachings herein may be incorporated with the teachings of these patent references will be apparent to those of ordinary skill in the art.

Versions of the present invention have application in conventional endoscopic and open surgical instrumentation as well as application in robotic-assisted surgery.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
    (a) an implantable band assembly, wherein the implantable band assembly comprises:
        (i) an inner band, wherein the inner band is configured to expand from a deflated configuration to an inflated configuration, and
        (ii) an outer band, wherein the outer band comprises a flexible biocompatible material positioned along an outer portion of the inner band;
    (b) a plurality of tabs in communication with the outer band, wherein the plurality of tabs comprise an elastomeric material, wherein the plurality of tabs are configured to be elastomerically flexible such that the tabs have elastic properties, wherein at least some of tabs of the plurality of tabs are symmetrically positioned along an outer surface of the outer band, wherein the plurality of tabs include at least an end tab and a pull tab;
    (c) a plurality of tissue matrices fixedly secured to the inner band, wherein at least one tissue matrix of the plurality of tissue matrices is attached to a portion of the inner band with a surgical adhesive, wherein the plurality of tissue matrices is configured to encourage tissue growth, wherein the plurality of tissue matrices comprise a plurality of trabeculae configured to promote tissue growth, wherein at least one tissue matrix of the plurality of tissue matrices is infused with a slurry of tissue to promote tissue growth, and wherein the plurality of tissue matrices comprises a plurality of discrete patches that are selectively positioned along an inner surface of the inner band in a spaced-apart relationship, wherein the plurality of discrete patches are positioned in a concentrated relationship in a region of the inner band that is susceptible to slippage;
    (d) a catheter;
    (e) an injection port, wherein the catheter is in fluid communication with the injection port; and
    (f) a fluid port in fluid communication with the catheter, wherein the fluid port is further in fluid communication with the inner band such that the fluid port is configured to deliver fluid from the catheter to the inner band.

* * * * *